(12) United States Patent
Nour et al.

(10) Patent No.: US 11,324,406 B1
(45) Date of Patent: May 10, 2022

(54) CONTACTLESS PHOTOPLETHYSMOGRAPHY FOR PHYSIOLOGICAL PARAMETER MEASUREMENT

(71) Applicant: King Abdulaziz University, Jeddah (SA)

(72) Inventors: Majid Nour, Jeddah (SA); Kemal Polat, Bolu (TR)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/363,418

(22) Filed: Jun. 30, 2021

(51) Int. Cl.
*A61B 5/0205* (2006.01)
*A61B 5/00* (2006.01)
*A61B 5/103* (2006.01)

(52) U.S. Cl.
CPC .......... *A61B 5/0205* (2013.01); *A61B 5/0022* (2013.01); *A61B 5/0077* (2013.01); *A61B 5/1032* (2013.01); *A61B 5/6816* (2013.01); *A61B 5/6826* (2013.01); *A61B 5/6828* (2013.01); *A61B 5/7264* (2013.01); *A61B 5/742* (2013.01)

(58) Field of Classification Search
None
See application file for complete search history.

(56) References Cited

U.S. PATENT DOCUMENTS

| | | |
|---|---|---|
| 10,398,314 B2 | 9/2019 | Zalevsky et al. |
| 2009/0209828 A1 | 8/2009 | Musin |
| 2016/0345832 A1 | 12/2016 | Pavagada Nagaraja et al. |
| 2018/0214088 A1* | 8/2018 | Newberry ............ A61B 5/6817 |
| 2020/0060584 A1 | 2/2020 | Musin |

FOREIGN PATENT DOCUMENTS

EP 3207862 A1 * 8/2017 ........... A61B 5/1176

OTHER PUBLICATIONS

Unakafov et al.—Using imaging photoplethysmography for heart rate estimation in non-human primates; PLOS ONE | https://doi.org/10.1371/journal.pone.0202581 Aug. 31, 2018 (Year: 2018).*
Lai et al.—Separation of color channels from conventional colonoscopy images improves deep neural network detection of polyps; Journal of Biomedical Optics; Jan. 2021 (Year: 2021).*
Fernandez et al. (A photoplethysmography smartphone-based method for heart ratevariability assessment: device model and breathing influences; Biomedical Signal Processing and Control 57; 2020) (Year: 2020).*

(Continued)

*Primary Examiner* — Jay B Shah
(74) *Attorney, Agent, or Firm* — WC&F IP

(57) ABSTRACT

Provided are systems and methods for determining a subject's physiological parameters such as heart rate, blood glucose level, variation in heart rate and/or oxygen saturation in a non-contact manner. A photoplethysmography (PPG) signal representing physiological parameter is obtained from a subject by a sensor that generates non-contact PPG signal in red, blue, green (RBG) components. The method further includes a step of analyzing the RBG components for simultaneously measuring the oxygen saturation level and any of the heart rate, blood glucose level or variation in heart rate of the subject.

7 Claims, 12 Drawing Sheets

(56) References Cited

OTHER PUBLICATIONS

Ding et al. (Measuring Oxygen Saturation With Smartphone Cameras Using Convolutional Neural Networks; IEEE Journal of Biomedical and Health Informatics, vol. 00, No. 00, 2018) (Year: 2018).*
Matsumura et al. Iphone 4s Photoplethymography; PLoS ONE • Mar. 2014 (Year: 2014).*
Nugraha et al: "Non-Contact Measurement of Blood Glucose based on Artificial Neural Network", International Journal of Computer Applications, vol. 76, No. 13, pp. 33-36, Aug. 2013.
Scalise: "Non Contact Heart Monitoring", INTECH, Jan. 25, 2012.
Verkruysse et al: "Calibration of Contactless Pulse Oximetry", Anathesia & Analgesla, vol. 124, No. 1, pp. 136-145, Jan. 2017.
Zhao et al: "Technology platforms for remote monitoring of vital signs in the new era of telemedicine", Expert Rev. Med. Devices Early Online, 2015.

\* cited by examiner

CONTACTLESS PHOTOPLETHYSMOGRAPHY FOR PHYSIOLOGICAL PARAMETER MEASUREMENT

FIELD OF THE INVENTION

The disclosure generally relates to a photoplethysmography (PPG) system and a method for determining at least one physiological parameter of a subject in a contactless manner by means of a PPG system. In particular, the disclosure provides a method of using such system for simultaneously determining one or more physiological parameters including blood glucose level, heart rate, changes in heart rate and/or oxygen saturation. The physiological parameter values are measured by obtaining at least one PPG signal without physical contact by processing an image reflected or transmitted from a subject's skin.

BACKGROUND

Photoplethysmography (PPG) is a noninvasive, electro-optical method that provides information about the volume of blood flowing in a test area of the body close to the skin. A photoplethysmography is obtained by illuminating the relevant area of the body and receiving the reflected or transmitted light signal. The use of PPG as a replacement of an invasive physiological vital sign measurement has become a routine practice in many places, especially in a hospital setting. To measure the heart rate and body temperature, a PPG signal is generally received by using a pulse oximeter which illuminates the skin and measures the changes in light absorption. A conventional pulse oximeter monitors the perfusion of blood to the dermis and subcutaneous tissue of the skin and is commonly worn on the wrist or a finger. In cases of shock (e.g., hypothermia), however, PPG can be obtained from a pulse oximeter placed on the head, with the most common sites being the earlobe, nasal septum and forehead (i.e., the parts of the body that are close to the arteries).

To use PPG, a protrusion in human body, such as a finger (index finger), is placed on one side of a light source with a wavelength of $\lambda$ and a photodetector to capture the light transmitted to the directly opposite side of the light source. A typical PPG signal consists of a large D.C. component that passes through the skin, muscle and bone without passing through the blood vessels and a small A.C. component that can pass through the blood vessels, including arterial blood vessels. Traditional PPG signal stream is typically obtained from a peripheral site such as the finger or other extremities by clamping, attaching or holding the sensor onto the target skin. The PPG system functions based on a normal physiological response; measuring the increasing amount of blood in the arteries immediately after systole, in which then it decreases the amount of light reflected or transmitted back accordingly. During diastole, the amount of blood in the arteries decreases, thus leading to an increase in light transmission. In a primary measurement site, 99% of the signal comes from the skin, muscle and bone, 0.9% from the veins and 0.1% from the arteries. Exemplary conventional PPG coupled with a sensor placed on a finger, either in a transmitted or reflective mode, are shown in FIG. 1A.

While commonly used PPG is obtained by some form of direct skin contact, recently developed remote PPG techniques allow measuring physiological processes such as heart rate in a contactless manner. Although some non-invasive techniques exist (e.g., near-infrared spectroscopy), obtaining and operating the remote blood glucose level measuring equipment may be expensive. To use such remote PPG techniques, sophisticated forms of devices containing sensors, cameras, computer-based analyzing machines and/or monitors are required. Thus, the current PPG techniques may only be suitable for uses in certain environments (e.g., clinic, hospital, research facility, etc.). In addition, the remote PPG techniques may not be readily available to other types of physiological measurement, such as blood glucose level or oxygen saturation. For patients with diabetes mellitus, which is a chronic incurable disease that causes an array of serious medical complications, it is critical to regularly monitor the glucose levels, multiple times a day to regulate blood glucose level by either adjusting or administering insulin accordingly. Of note, there is neither a standardized measurement setup nor an agreement on algorithms for the remote sensors that are being studied for this particular usage. In addition, none of the methods or systems known in the art can simultaneously measure and process the result of more than one physiological parameter such as blood glucose rate, heart rate and oxygen saturation in a contactless manner.

Thus, there is a need in the art for an improved remote physiological parameter measuring system with simple and accurate measuring ability and flexibility to provide access to the data in a cost-efficient manner.

SUMMARY OF THE INVENTION

The present invention relates to a system and a method for determining physiological parameters in a contactless manner. The system includes at least one imaging device or sensor with a capacity to obtain the variance of at least three different colors (i.e., red, green and blue) in at least one image or video, at least one light source, at least one computer for analysis and at least one monitor for data display. Another object of the invention is newly formed algorithms providing analysis of various physiological measurements such as a heart rate, blood glucose measurement, changes in heart rate and/or oxygen saturation level. One of the advantageous features of the present invention includes a remote and non-invasive method of measurement, in which the results can be monitored in real time, providing an alternative to conventional pulse oximeters and blood glucose meters without the need for a device, needle or blood sample. The method described in the present invention can be used at home or in a hospital. The system described herein for implementing the method provides high reliability, ease of access, user-friendly remote data transferring ability through wireless communication, capacity for continuous monitoring and cost-effective means of physiological parameter measurement.

One aspect of the disclosure provides a system for implementing a method of measuring one or more physiological parameters. In various embodiments, a system includes a sensor or a camera configured to obtain at least one image and/or video composed of three colors (i.e., red, green and blue (RGB)) of one or more of a face, finger, palm or earlobe of a subject; and at least one computer software to implement algorithms to decompose the RGB image into red, green and blue band components so that the one or more of physiological parameters selected from the blood glucose level, heart rate and variation in heart rate are measured based on the green band component image while the level of oxygen saturation is measured based on the blue and red band components; and at least one monitor or screen to display the one or more of the blood glucose level, heart rate, variation in heart rate and/or oxygen saturation.

Another aspect of the disclosure provides a method of determining one or more of physiological parameters including a blood glucose level, heart rate, variation in heart rate or oxygen consumption in a contactless manner, comprising: i) obtaining at least one image and/or video of the subject at a plurality of areas of the subject's body where the areas of the subject's body are selected from the group consisting of a head of the subject, an arm of the subject and a leg of the subject; ii) decomposing the at least one image and/or video into red, green and blue (RGB) band components; determining the one or more of the blood glucose level, heart rate, variation in heart rate and/or oxygen saturation; and iii) displaying the determined physiological parameters. In some embodiments, the step of decomposing is performed using at least one algorithm developed by a classical machine learning. In some embodiments, the decomposing step may include a deep learning-based algorithm.

In another aspect, the present disclosure relates to a method of simultaneously determining at least two physiological parameters including the blood glucose level, heart rate or variation in heart rate and the oxygen consumption in a contactless manner, comprising: i) obtaining at least one image and/or video of the subject at a plurality of areas of the subject's body where the areas of the subject's body are selected from the group consisting of a head of the subject, an arm of the subject and a leg of the subject; ii) decomposing the at least one image and/or video into red, green and blue (RGB) band components; iii) determining the one or more of the blood glucose level, heart rate and/or variation in heart rate; iv) simultaneously determining the oxygen saturation; and v) displaying the physiological parameters. In preferred embodiments, the physiological parameters including the blood glucose level, heart rate and variation in heart rate are determined based on the green band image whereas the oxygen saturation is based on the blue and red band image. In some embodiments, the step of decomposing is performed using at least one algorithm developed by classical machine learning. In some embodiments, the decomposing step may include a deep learning-based algorithm. In other embodiments, the decomposing step includes algorithms developed by both a classical machine learning and deep learning.

Additional features and advantages of the present invention will be set forth in the description of disclosure that follows, and in part will be apparent from the description of may be learned by practice of the disclosure. The disclosure will be realized and attained by the systems and methods particularly pointed out in the written description and claims hereof.

DETAILED DESCRIPTION

The present disclosure relates to a photoplethysmography (PPG) system for determining at least one physiological parameter in a contactless manner. The system includes one or more sensors and/or cameras configured to obtain one or more images and/or videos of a subject; one or more computers with software for analyzing the received images or videos by processing algorithms; and one or more monitors or screens for displaying the analyzed physiological parameter data for a visual display. The present disclosure also includes a method for determining at least one physiological parameter in a contactless manner. The method includes obtaining at least one image and/or video of at least one area of the subject's body, decomposing the image and/or video into three or more color channel components, determining one or more physiological parameters and visually displaying the analyzed physiological parameters in real time.

The PPG system for implementing a method of measuring one or more physiological parameters includes a sensor or a camera configured to obtain at least three-color (i.e., red, green and blue (RGB)) image and/or video of one or more of a face, finger, palm or earlobe of a subject. In some embodiments, the sensor or camera may obtain at least one image and/or video of any areas of the subject's body including a head (i.e., any parts of the head such as a face, earlobe, nose, cheek, forehead, etc.), an arm (i.e., any parts of the arm including the hand such as a finger, palm, etc.) and a leg (i.e., any parts of the leg including the foot such as a toe, thigh, shin, etc.).

Figure 1A:
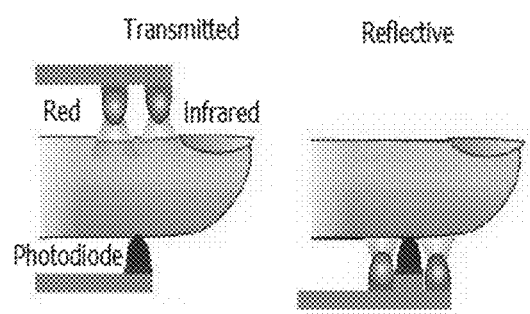
FIG. 1A is a schematic representation of the conductive or transmitted (left) and reflective (right) sensors.
Figure 1B:
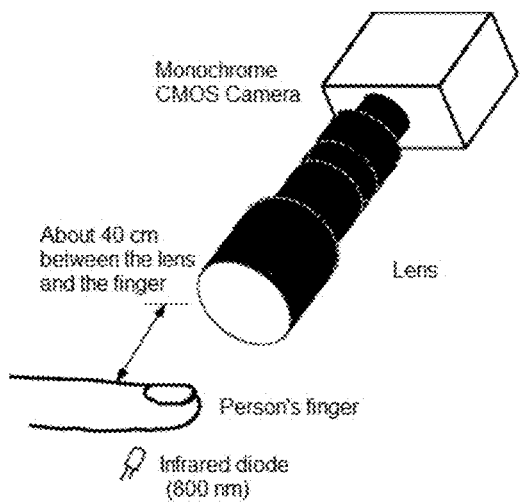
FIG. 1B is a schematic representation of photoplethysmography imaging system in a transmission mode.
Figure 2A:
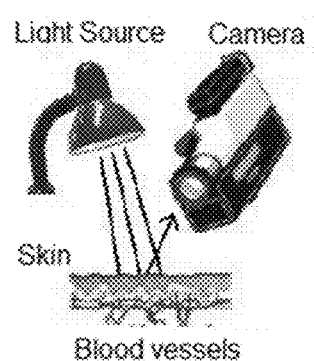
FIG. 2A is a schematic representation of photoplethysmography imaging system in a reflection mode.
Figure 2B:
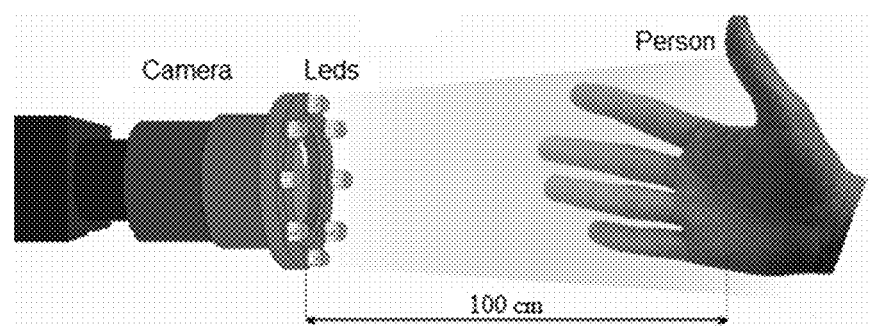
FIG. 2B is a schematic representation of a photoplethysmography imaging system in a reflection mode including a light source mounted on a camera.

FIG. 1B and FIG. 2A-B illustrate exemplary PPG systems for obtaining the images through the system's sensors in the form of a camera. The camera may be in a transmission mode or on the principle of a reflection mode for obtaining at least one PPG signal from the image of the light-emitting diode transmitted to the camera by passing through the finger (FIG. 1B). Alternatively, in some embodiments, the PPG sensors or video cameras may be in a reflection mode (FIG. 2A-2B).

As used herein, "light source" refers to any apparatus or device that makes light, whether visible or infrared light, including, among other things, directly or indirectly provided light as well as electromagnetic radiation of any frequency. In some embodiments, light-emitting diodes (LED) is used. In some embodiments, the light source may provide light at an infrared range encompassing 600-1300 nm, preferably 700-1000 nm, more preferably 750-950 nm. As used herein, "sensor" or "detector" includes any device of a photodiode, phototransistor, charge-coupled device (CCD), thermopile detector and/or complementary metal-oxide semiconductor (CMOS) sensors, which may be used in both transmission and reflection modes.

Figure 3:
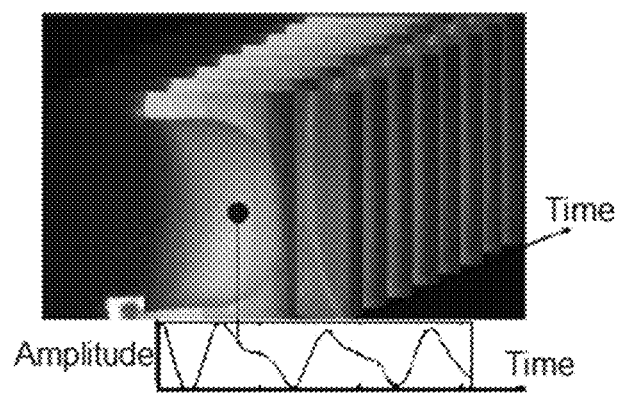
FIG. 3 shows a photoplethysmography signal derived from any point of video frames in the time domain.

As used herein, "sensor" and "camera" may be interchangeably used in some embodiments. Some exemplary cameras include, but are not limited to, a digital camera, a mobile camera, a video camera, a light sensor or an array of light sensors, an imaging system, a light field camera or plenoptic camera, a time-of flight camera, an optical instrument that records images and a computer or circuit connected camera. In some implementations, a monochrome CMOS sensor camera is used with a full resolution of 1280×1024. In other embodiments, the videos are recorded by a digital single lens reflex (DSLR) camera with a 960× 729 resolution setting. In some embodiments, the sensor or camera may not capture all of the pixels for a full resolution in the formation of a PPG signal. For the formation of a PPG signal, a sufficient amount of the pixel region, in which the PPG signal obtained from a portion of the subject's skin may vary. For example, a sufficient amount of 20×20 pixels in the sequence of video picture frames in the region where the finger (index finger) tip is located may be collected (FIG. 3). By achieving the average brightness level from the video picture frame to the frame of the 20×20 Pixel region on the time axis, PPG signal is generated with cameras recording of 25-30 picture frames per second.

In exemplary embodiments, the camera or video camera with a CMOS sensor may have three or more color channels. The three-color channels may include red, green and blue (RGB) colors. In some embodiments, the sensor of the camera includes other color channels, for example, 4 or 5 or more colors (e.g., red, orange, green, cyan and blue). As used herein, "color channels" or "color band components" refers to a set of pixels that is most sensitive to particular ranges of wavelength of light. Generally, the color range wavelength is between 440-485 nm. The term "green" refers to a set of pixels that is most sensitive to a range of wavelength encompassing 538-544 nm. The term "blue" refers to a set of pixels that is most sensitive to a range of wavelength encompassing 440-485 nm. The term "red" refers to a set of pixels that is most sensitive to a range of wavelength encompassing 630-700 nm. The term "orange" refers to a set of pixels that is most sensitive to a range of wavelength encompassing 548-562 nm. The term "cyan" refers to a set of pixels that is most sensitive to a range of wavelength encompassing 505-533 nm.

The PPG system further includes at least one computer with at least one software to implement algorithms to decompose the RGB image into red, green and blue band components so that one or more of physiological parameters selected from the blood glucose level, heart rate and variation in heart rate are measured based on the green band component image while the level of oxygen saturation is measured based on the blue and red band components; and at least one monitor or screen to visually display one or more of the blood glucose level, heart rate, variation in heart rate and oxygen saturation. As used herein, "computer" includes any computational device that performs logical and arithmetic operations. For example, in some cases, a computer includes an electronic computational device, such as an integrated circuit, a microprocessor, a mobile computing device, a laptop computer, a tablet computer, a personal computer or a mainframe computer. In some cases, a computer comprises a central processing unit, an arithmetic logic unit, a memory unit, a control unit and at least one software that controls actions of other components of the computer so that encoded steps of a program are executed in a sequence. The computer may also include a screen or monitor for visually displaying the computer analyzed results. However, a human is not a computer, as the term is used herein.

In some embodiments, the PPG system described herein is used for determining at least one of a blood glucose level, heart rate, variation in heart rate or oxygen consumption in a contactless manner. The method includes steps of obtaining at least one image and/or video of the subject at a plurality of areas of the subject's body where the areas of the subject's body are selected from the group consisting of a head of the subject, an arm of the subject and a leg of the subject, decomposing the at least one image and/or video into red, green and blue (RGB) band components, determining one or more of the blood glucose level, heart rate, variation in heart rate and/or oxygen saturation, and displaying the physiological parameters. In some embodiments, the step of decomposing is performed using at least one algorithm developed by a classical machine learning. In some embodiments, the decomposing step may include a deep learning-based algorithm. As used herein, "decomposing" refers to an image decomposition for separating structure from a given image by preserving edge-like structure components and removing fine-scale details without prior information. The image decomposition by using a set of algorithms is to break an image data down into smaller and more refined components, for example, colors or shapes.

In preferred embodiments, the PPG system is used for simultaneously determining at least two physiological parameters including the blood glucose level, heart rate, variation in heart rate and the oxygen consumption in a contactless manner. The method includes steps of obtaining at least one image and/or video of the subject at a plurality of areas of the subject's body where the areas of the subject's body are selected from the group consisting of a head of the subject, an arm of the subject and a leg of the subject, decomposing the at least one image and/or video into red, green and blue (RGB) band components, determining one or more of the blood glucose level, heart rate and/or variation in heart rate, simultaneously determining the oxygen saturation and displaying the physiological parameters. In preferred embodiments, the physiological parameters including the blood glucose level, heart rate and variation in heart rate are determined based on the green band component whereas the oxygen saturation is based on the blue band and red band components. In some embodiments, the step of decomposing is performed using at least one algorithm developed by a classical machine learning. In some embodiments, the decomposing step may include at least one deep learning-based algorithm. In some embodiments, all of the described physiological parameters (i.e., blood glucose level, heart rate, variation in heart rate and oxygen consumption) may be determined at the same time. Alternatively, in other embodiments, the blood glucose level and oxygen consumption may be determined at a given time. In yet another embodiment, the heart rate and oxygen consumption may be measured at a given time.

According to a preferred embodiment, a web camera is used to obtain PPG signals without contact. Face, palm, and finger images and/or camera recordings may be collected to get the PPG signal without contact. Alternatively, other regions that provide a better PPG signal may be determined and the images or videos may also be taken with a mobile phone with a camera. In some cases, one or more computers are programmed for communicating over a network. For example, one or more computers are programed for network communication in accordance with the internet protocol suit or wireless standard. Alternatively, the system and method may include communication between at least one camera and at least one computer through one or more wirings, routers, cables or computer ports. To obtain the image or video, the camera or sensor is positioned about 10-120 cm, preferably about 15-110 cm, more preferably about 18-100 cm from the skin of the subject. In some embodiments, the distance between the sensor and the skin of the subject may be about 30-80 cm, preferably about 40-70 cm, more preferably about 50-60 cm.

Figure 4:
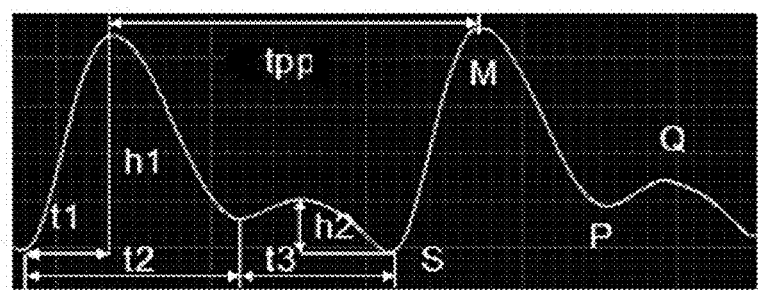
FIG. 4 shows a standard PPG photoplethysmography and feature points for measuring a periodic heartbeat.

Referring to FIG. 4, in some embodiments, the PPG system measures the heartbeat based on the PPG signal produced by the periodic beat of the heart. The PPG signal is generated from a transmission or reflective mode on a patient's cardiovascular (i.e., heart and blood vessels) information based on changes in blood flow in the veins affecting vascular flexibility and blood viscosity (resistance to fluidity). In a typical PPG signal, the part from point S to point M is the fast throw phase, and the part from point M to point P is the delay phase. M is the main peak of the signal. At this point, blood pressure (B.P.) is at its highest value in the entire period. Another peak is the dichrotic wave, which reflects the harmony of the arteries called Q. The P point is called the dichrotic notch. Heart rate is obtained from the time between the two main peaks (T.P.P.). The M-Q time interval is an index of arteriosclerosis (atherosclerosis). However, due to the presence of various factors, feature points for the true PPG signal are difficult to obtain directly.

Figure 5A:
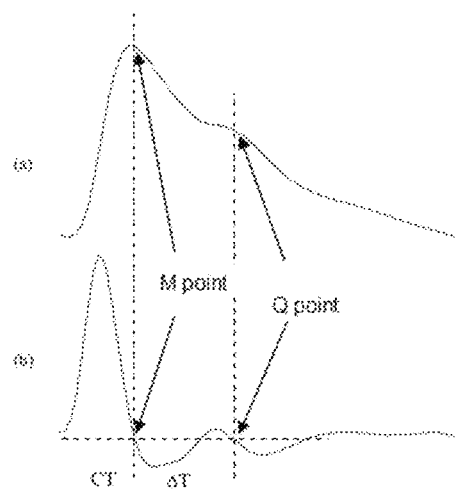
FIG. 5A shows a signal measurement of (a) the original PPG signal and (b) the first derivative of PPG signal.
Figure 5B:
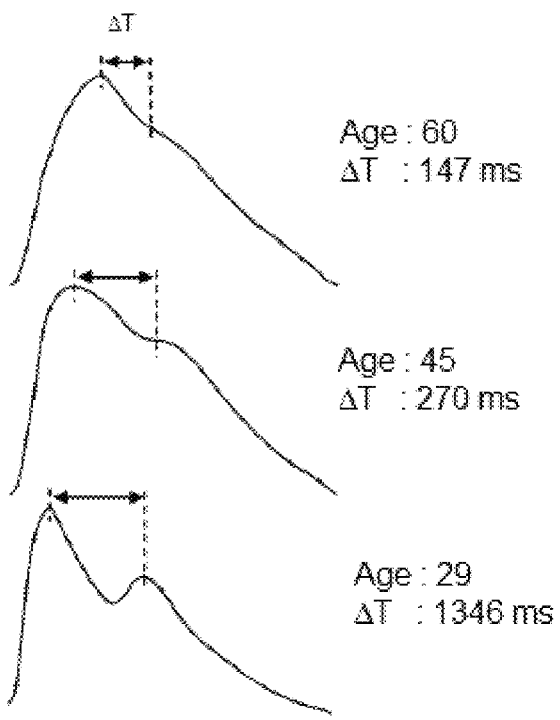
FIG. 5B shows the changes in PPG signals with person's age.
Figure 6:
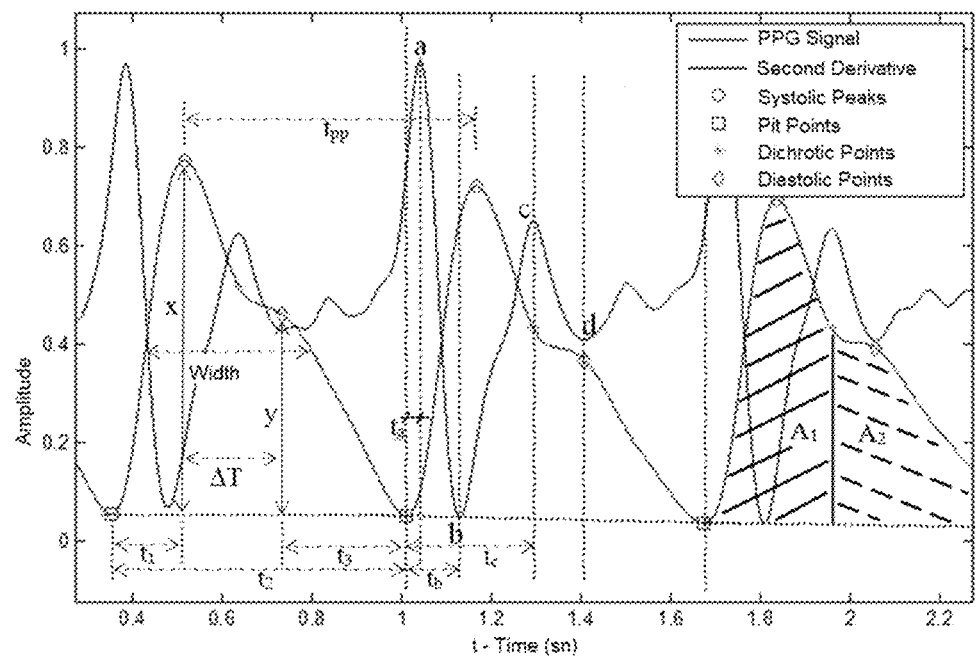
FIG. 6 shows the original PPG signal, the second derivative of PPG signal and characteristic feature points of the two PPG signals.

To distinguish the feature points of the PPG signal, the first derivative of the PPG signal is used in the PPG signal to find some basic features such as M point, Q point, M point time (C.T.), and M point and Q point time interval ($\Delta T$), as shown in FIG. 5A. The second derivative of the PPG signal is more useful than the first derivative of the PPG signal as it is an indicative of acceleration in finger blood flow. The point P between Point M and Point Q is not always formed as a complete notch and varies depending on the person's age. At this point, it is easy to use the second derivative of the PPG signal to determine the P point. In addition, characteristic points a, b, c, d, e, as shown in FIG. 5B, on the second derivative provide ease in determining people's individual characteristics. As shown in FIG. 6, x (systolic peak), y (diastolic peak), y/x, (x−y)/x, tpp (peak to peak time interval), t1 (systolic peak time), t2 (P.P.G. signal pulse time), $\Delta T$ (time between systolic peak and diastolic peak), width (pulse width half the height of systolic peak), A2/A1 (ratio of areas left and right of dichroic point in P.P.G. signal), b/a, c/a, (b+c)/a, t1/t2, $\Delta T/t2$, t1/x (systolic peak output slope), y/t3 (diastolic peak fall slope), ta (second derivative a point time), tb (second derivative b point time) and tc (second derivative c point time) 20 characteristic features of the PPG signal can be found using the second derivative of the PPG signal.

By utilizing the pulse transit time (PTT) in the human body, PPG technology can be also used for blood pressure measurements. Additionally, thermal sensor cameras may be used for measuring human facial blood flow, heart rate and respiratory rate. Any devices that support independent component analysis (ICA) to separate three or more channel components may be used. ICA is a blind source separation technique used to reveal source signals, independent of a dataset consisting of linear mixtures of basic sources. ICA may be applied to reduce motion artifacts in PPG measurements. A webcam may be used to regulate human heart rate viability (KDH), discharge cycle, respiratory rate and other physiological indicators. Other exemplary physiological conditions applicable to the present invention include atrial fibrillation, blood loss, and cardiac autonomic function. Color changes on the skin can be examined by optical monitoring of the skin with a digital camera. Color changes are caused by cardiac signals and pulsatile signals. The illumination of an area with a white LED) mobile phone flash is also considered and this imaging can be defined as a reflective PPG imaging.

Figure 7:
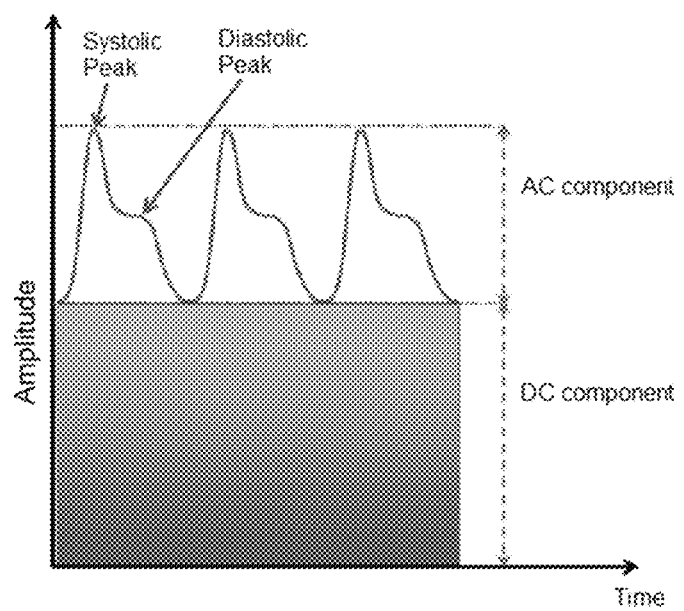
FIG. 7 shows A.C. and D.C. components of the photoplethysmography signal obtained from a finger.

Referring to FIG. 7, the P.P.G. signal obtained from a biological tissue (finger) consists of alternating current (A.C.) and direct current (D.C.) components. The D.C. component offsets the constant voltage amplitude and can be detected according to the nature of the material through which the light passes. The A.C. or pulsatile component is the heart rate whose arterial blood volume is dependent on the pulse. The shape of the A.C. signal is an indicator of cardiac performance and vascular compliance. AC component amplitude is 1-2% of the DC value. Using the PPG system, the heartbeat can be monitored with light absorption differences in the systole and diastole of the pumped blood. Some changes have been made in PPG-based pulse oximeters to develop experimental setups for the noninvasive measurement of blood glucose. Noninvasive measurement of blood sugar is done by sending a beam of light to the finger and analyzing the light reflected from the finger. The absorption of light by the skin depends on various components in the blood, such as water, hemoglobin, fat, and glucose. However, the absorption of light by these components depends largely on the wavelength of the transmitted light. At a given wavelength, the bond between the atoms of the component vibrates, and the light is absorbed. Glucose concentration can be determined by analysis of changes in wavelength or intensity of passing light. The blood sugar content can be calculated by measuring with infrared light of different wavelengths (from 700 nm to 2500 nm), from the thin part of the body segment (usually fingertip).

Figure 8:
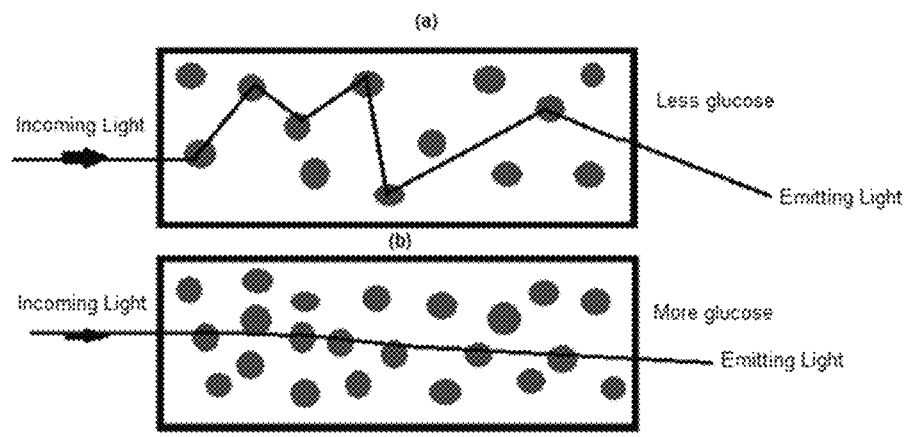
FIG. 8 is a schematic representation of the effect of glucose in light emission with a low glucose level (A) or with a high glucose level (B) in blood.

Referring to FIG. 8, with a low glucose level in blood, the light beam travels along optical paths resulting more light scatters and a smaller peak. However, when more glucose in the blood vessels, the light needs less optical path due to less scattering. This results in higher hills at the outlet. An increase in the intensity of light transmitted in accordance with the glucose concentration can be achieved. The improved setup uses the attenuation of light of different wavelengths, where the light emission changes with the sugar content in the red blood cell in the blood. Blood absorption depends on blood sugar level.

In some embodiments, the heart rate, variation in heart rate, blood glucose level and oxygen saturation can all be measured simultaneously. In other embodiments, other physiological parameters, such as body temperature, serum levels of various stress hormones, immunological functions may be assessed. For example, in some embodiments, other monitoring devices, including invasive, non-invasive, in contact and/or contactless devices, may optionally or simultaneously be used. In these embodiments, any mobile software, transferred to mobile phones, web pages, tablet computers, and/or the relevant doctor may be instantly displayed. The system and methods may be used at home as well as in a hospital setting. In the case of use at home or any other places, non-contact PPG signals may be obtained from images or videos of a finger, palm, earlobe, face using a webcam, and physiological variables recorded via a mobile device are presented continuously on the monitors of smartphones and computers.

The system disclosed herein features such properties as high reliability, ease of use, ease of access, remote data transfer through wireless communication, continuous monitoring of disease state, and mobile and inexpensive software.

EXAMPLE 1

Comparison Between PPG with Experimental Data

Figure 9:
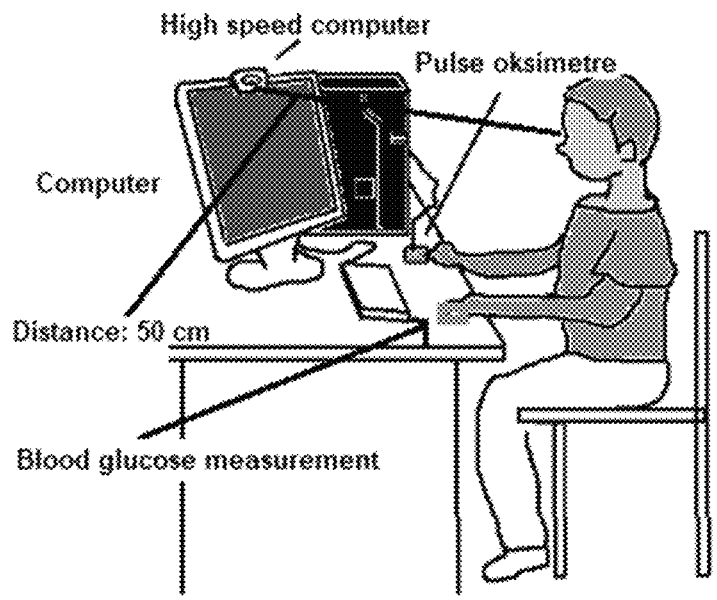
FIG. 9 is a schematic representation of the blood glucose level and pulse data from over 500 people in total, approximately 100 people from each age group.

Data acquisition is carried out at Sakarya University, Faculty of Medicine. The data is taken over 500 people in total, approximately 100 people from each age group. The mechanism for data acquisition is given in FIG. 9. This setup includes a high-speed camera, a computer, a pulse oximeter, and a blood glucose meter. The purpose of the establishment of this mechanism is to estimate the physiological parameters from the healthy or sick person by using the pulse oximeter and blood glucose meter simultaneously with the camera. Recording the real contact PPG signals and the actual blood glucose value of that person and the physiological parameters are estimated by the proposed method. The performance of the system is tested by comparing it with actual values. In this setup, two camera recordings were made to estimate the person's blood glucose measurement.

In the first recording, the camera recorded while the incoming person is hungry, then the camera recorded again 2 hours after the person arriving has eaten. Recording times are between 1 and 2 minutes. The camera images are taken separately from the human face, ear (right), palm (right), and index finger (right). The distance between the webcam and the person is adjusted to be 50 cm. Images are recorded in A.V.I. (Audio Video Interleave) format using 200 fps (frame per second). With the high-speed camera, images are recorded in different light environments. These environments are daylight and spotlight. The reason for this process is to design an image filter to block out external light while recording. Data is taken in a sitting position, in a calm state, without any activity. Color camera recordings are taken from the people with the webcam (When open, 1 to 2 minutes, is taken separately from four regions). Camera recordings are taken for two different light systems, namely daylight and spotlight (between 1 and 2 minutes, it is taken separately from four regions). Color camera recordings are taken 2 hours after the person has eaten (1 to 2 minutes, is taken separately from four regions). While the camera records are taken from the people with the webcam, a finger-type pulse oximeter device is attached to the person, and the contact PPG signal is recorded instantly. (It is used to measure oxygen saturation in the blood, heart rate value, and heart rate change values). At the same time, glucose rates are recorded by attaching a blood glucose meter to the person both when the person is hungry and when the person is full (after 2 hours).

EXAMPLE 2

Estimation of Human Physiologic Parameters

Figure 10:
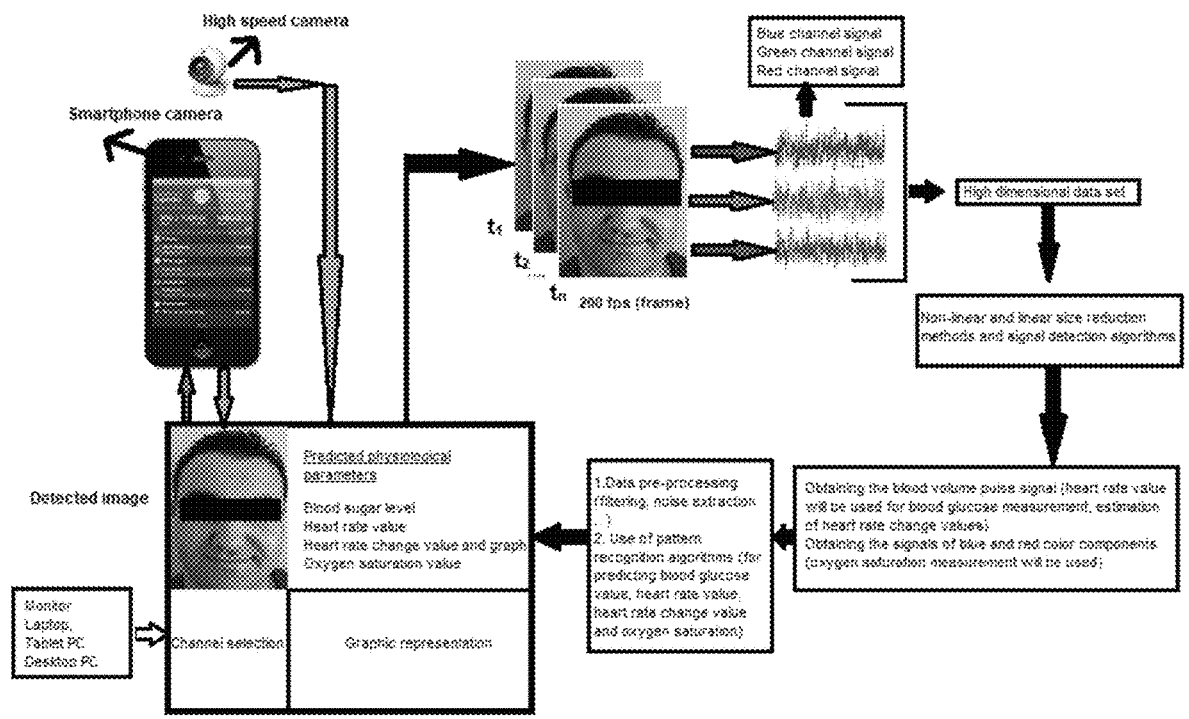
FIG. 10 is a block scheme of a proposed method of measuring the physiological parameters such as a blood glucose level, heart rate and oxygen saturation, from the non-contact photoplethysmography signals using a web camera.
Figure 11:
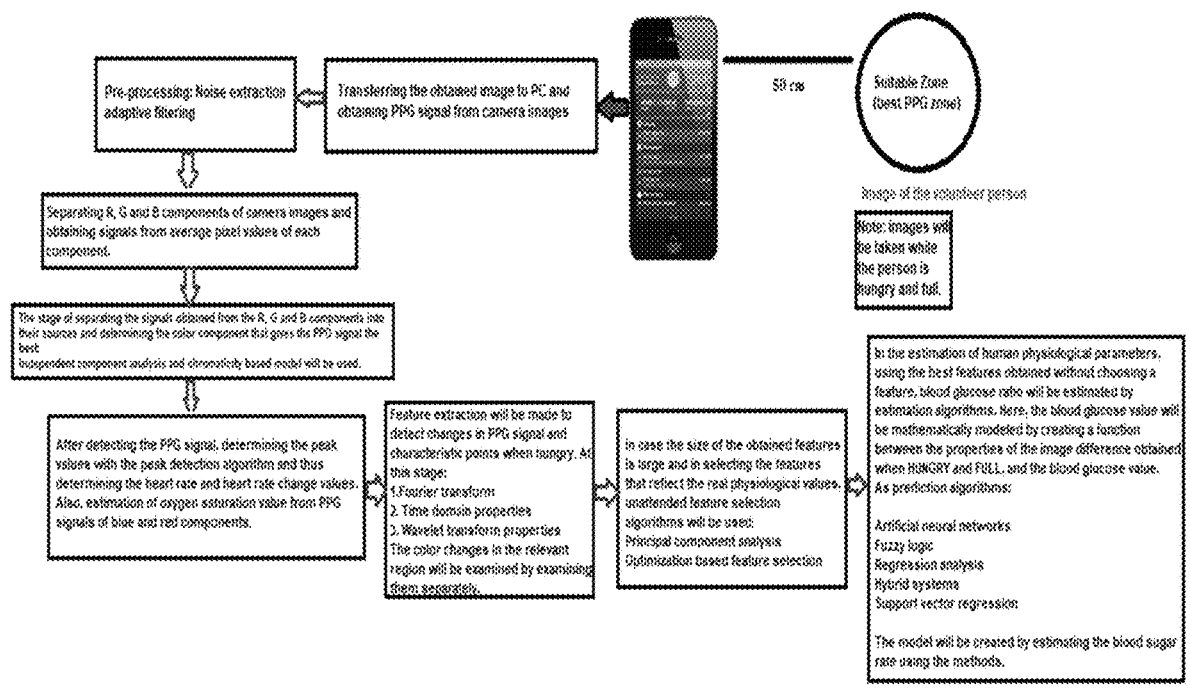
FIG. 11 is a detailed block diagram of a proposed method for measuring the physiological parameters such as a blood glucose level, heart rate and oxygen saturation from the non-contact photoplethysmography signals using a web camera.
Figure 12A:
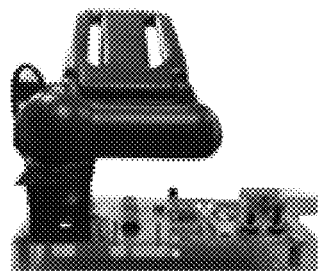
FIG. 12A-B show (A) a side view and (B) a perspective view of an exemplary photoplethysmography data acquisition card attached to a webcam.
Figure 12B:
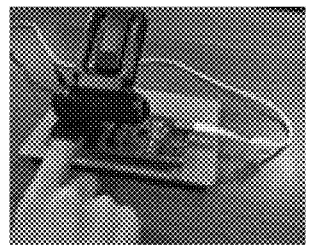
Figure 12C:
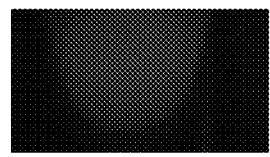
FIG. 12C shows an A-frame image obtained with the webcam of FIG. 12A-B.

FIG. 10 shows a block diagram of non-contact acquisition of PPG signal using a high-speed camera and estimation of human physiological parameters. In this block diagram, firstly, images of the human face, finger, palm, or ear are sent to the computer for wireless processing using a high-speed camera or camera belonging to a smartphone. The operations to be done on the computer are listed below:

a) First, object detection algorithms are used to detect the face, finger, palm, or ear from the images obtained from the camera. And the relevant region is determined (Region of Interest-ROI)

b) Images obtained at 200 fps are combined to produce color RGB video recording.

c) Obtaining red, green, and blue color bands from RGB camera images by image processing.

d) A 3-dimensional data matrix is obtained by combining the obtained color components (increase to large size)

e) This matrix is reduced to one dimension by applying dimension reduction methods. As methods of size reduction, basic component analysis, independent component analysis, linear decomposition analysis, Isomap, Laplace Eigenmap, locally joining method and with the new size reduction methods to be suggested, the PPG signal which is the only size downloaded is obtained (size reduction methods).

f) A mathematical model is created by examining the relationship between the PPG signal found by size reduction methods and the green band image signals (Regression methods).

g) Since it gives the PPG signal without contact with the image signals of the green band, the signals belonging to this band are used in the prediction of blood glucose ratio, heart rate value estimation, and heart rate change values. A non-contact PPG signal is obtained by taking camera images while the person is hungry, and the blood glucose ratio is estimated by establishing a relationship between the blood sugar rate and PPG signal change. Then, 2 hours after the person has eaten, the camera is recorded again, and the same operations are done while full. From the PPG signal changes obtained when hungry and full, the person's blood sugar rate is estimated by mathematical or intuitive methods. Linear and nonlinear regression methods are tried as mathematical methods, and the best method is determined. The instantaneous heart rate value is found by calculating the peaks of the non-contact PPG signal with peak detection algorithms and calculating the periods between two peaks. The heart rate change value graph is obtained by combining the obtained heart rates to obtain a heart rate change signal.

h) The oxygen saturation value in the blood is obtained by a mathematical model between the blue and red color bands' image signals and the oxygen saturation in the blood. If explained in detail:

Proportional $SpO_2$ measurement is made by comparing the red and blue bands. The blue band is an indication of the wavelength of infrared light used in conventional pulse oximetry $SpO_2$ measurement. Standard deviations of the red and blue bands at each time point were used as A.C. signals. D.C. components were calculated as the red and blue band average intensities at each time point. Proportional oxygen saturation is calculated according to the formula (equation 2):

$$SpO_2 = A - B \frac{AC_{RED}/DC_{RED}}{AC_{BLUE}/DC_{BLUE}} \qquad (2)$$

Parameters A and B are found by substituting the SpO$_2$ value obtained by using a commercial pulse oximeter and finding the best linear equation with the MATLAB Curve Fitting Toolbox.

i) Signal processing and pattern recognition algorithms are used to estimate human physiological parameter values using a camera image.

Image processing algorithms: R.O.I. detection algorithm, face detection algorithm, palm detection algorithm, finger detection algorithm, and ear detection algorithms are used, and the proposed system is automated with these developed algorithms.

Signal processing algorithms: Filtering algorithm, noise extraction from image and signal, peak detection algorithm in PPG signal, obtaining red, green, and blue band signals from RGB color images.

Feature extraction algorithms: By extracting properties from the PPG signal in the time and frequency domain, the relationships between physiological parameters are studied. The Methods to be Used:

Fast Fourier Transform
Short time Fourier Transform
Wavelet Transform
Subspace based transformation methods
Experimental mode decomposition
Nonparametric spectral analysis methods
Feature selection algorithms: Feature selection algorithms are used to select unrelated and unrelated features between the extracted features and physiological parameters after feature extraction from the contactless PPG signal and to reduce the computational cost.

Methods to Use:
Information gain-based feature selection method
Kernel-based feature selection method
Forward and backward sequential feature selection methods
Wrapper feature selection method
Filter based feature selection method.
Common information gain-based feature selection method
Variance based feature selection method.

Prediction algorithms: Regression and prediction algorithms are used to estimate physiological parameters from the non-contact PPG signal.

Methods to Use:
Curve fitting algorithms (MATLAB)
Linear regression algorithms
Nonlinear regression methods
Artificial neural networks
Fuzzy logic
Neural-fuzzy logic network-based hybrid systems
Support vector machines Smartphones, tablet computers, web pages, and devices using mobile software can be used to view the findings and values obtained after the estimation of human physiological parameter values. In this last stage, the values calculated on the computer are transmitted instantly to smartphones, tablet computers, web pages, and devices using mobile software via wireless communication after they are also displayed on the computer.

EXAMPLE 3

Results

With this application interface, PPG signals obtained from people's finger images are drawn in real-time and can be recorded to the computer whenever desired. The non-contact PPG signal was obtained by taking the red color layer into consideration in the camera images and obtaining the time change of the average brightness level. In addition, this application interface allows to mix the red, green, and blue color layers in the color finger images used while obtaining the non-contact PPG signal.

A probe emits at least two different light frequencies, such as by light-generating diodes (LEDs) and such emitted light is detected by at least one light detector, such as a photo-diode detector. A general-purpose computer or a special purpose computer is employed to perform complex mathematical computations based, typically, on the signal intensity and timing from the at least one pulse oximeter probe, and on signals from the light detectors of each probe. Proper analysis by software programming in such general-purpose computer or special purpose computer outputs results to a display, printer, etc. that suggests or indicates (depending on relative differences in the signal, and upon other conditions) whether blood flow and/or volume has changed in a selected body area.

EXAMPLE 4

The basic idea in blood glucose measurement, glucose in the blood, comes from the principle of absorbing very high amounts of infrared light from skin tissue. Approximately 15% is absorbed by the skin. In the presence of dark light as a background, the bloodless lesson tissue appears as dark lines, so all blood vessels reflect approximately ten times less light than the remaining tissue. Due to the higher wavelength of the transmitted light (greater than 940 nm), most of the light is sent to the other side of the finger and detected by the photodetector. The other part of infrared light is reflected from the tissues and the rest of the blood (wavelengths from 700 nm to 1300 nm because the blood has a very high absorption band). The PPG signal is obtained according to the pulsatile (percussion) component of arterial blood flow. However, this waveform contains both the D.C. component (made up of tissue, vein, and artery) and the A.C. component (arterial is made up of the pulsatile nature of blood). A.C. component is needed to achieve glucose level in blood. The following equation is used to remove the D.C. component from the PPG signal [30, 31].

$$\Delta OD_\lambda = \log\left[1 + \left(\frac{\Delta I_\lambda(t_i)}{I_\lambda(t_{i+1})}\right)\right] \quad (1)$$

Wherein, the $\Delta OD_\lambda$ is the difference in optical density between; $\Delta I_\lambda(t_i)$, $t_i$ is the instant pulsatile component. $I_\lambda(t_{i+1})$, $t_{i+1}$ is the intensity of light at the moment.

Depending on whether the person is hungry or full, a mathematical function is created with the features extracted from the PPG signal obtained without contact with the blood sugar value.

EXAMPLE 5

Exemplary algorithms used in the present disclosure are listed herein.

TABLE 1

ROI detection pseudocode

Input: image
Output: bounding box
for each area I the image do

TABLE 1-continued

ROI detection pseudocode

```
1- Extract features
2- Find local saliency
3- Determine area points and background points
4- Calculate background and foreground ratio
5- Find borders of foreground object and bounding box coordinates
end
return bounding box coordinates
```

TABLE 2

Face detection pseudocode

```
Input: image
Output: image with face borders
do 1- convert image to pyramid form
   2- calculate image integrals
   for each single images in pyramid do
      1- Calculate face indicators
      2- Filter detection sub-window
      3- Accumulate filter outputs
   end
   if sub-window passed all stages
      accept as face
end
```

TABLE 3

Palm detection algorithm

```
Input: image
Output: image with palm borders
do 1- convert image to pyramid form
   2- calculate image integrals
   for each single images in pyramid do
      1- Extract features for palm detection
      2- Calculate palm indicators
      3- Filter detection sub-window
      4- Accumulate filter outputs
   end
   if sub-window passed all stages
      accept as palm
end
```

TABLE 4

Finger detection algorithm

```
Input: image
Output: image with finger borders
do 1- convert image to pyramid form
   2- calculate image integrals
   for each single images in pyramid do
      1- Extract features for finger detection
      2- Calculate finger indicators
      3- Filter detection sub-window
      4- Accumulate filter outputs
   end
   if sub-window passed all stages
      accept as finger
end
```

TABLE 5

Ear detection algorithm

```
Input: image
Output: image with ear borders
do 1- convert image to pyramid form
   2- calculate image integrals
```

TABLE 5-continued

Ear detection algorithm

```
   for each single images in pyramid do
      1- Extract features for ear detection
      2- Calculate ear indicators
      3- Filter detection sub-window
      4- Accumulate filter outputs
   end
   if sub-window passed all stages
      accept as ear
end
```

TABLE 6

Low pass filtering algorithm

```
Input: image
Output: image with low frequency
for each pixel do
   1- Find pixel value
   2- Calculate neighborhood
   3- Check current pixel value and neighbor values
   4- Determine the rises
   5- Suppress high transitions
end
```

TABLE 7

Noise extraction from image and signal

```
Input: image or signal
Output: image or signal without noise
   1- Determine template to create regions
for each region do
   1- Find mean value
   2- Find median value
   3- Determine noise according to mean and median
   4- Remove noise
end
```

TABLE 8

Peak detection algorithm in PPG signal

```
Input: PPG signal
Output: image or signal without noise
   1- Save first value as a peak value
   2- Read current value and compare peak value
   if current value > peak value
      peak value=current value
   else
      peak value=peak value
   end
```

TABLE 9

Obtaining red, green, and blue band signals from RGB color images

```
Input: Image
Output: red, Green, and Blue components
   1- Red component = Image (:,:,1)
   2- Green component = Image (:,:,2)
   3- Blue component = Image (:,:,3)
return Red component, Green component, Blue component
```

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

ACKNOWLEDGMENT

The authors extend their appreciation to the Deputyship for Research & Innovation, Ministry of Education in Saudi Arabia for funding this research work through the project number (2021-036) and King Abdulaziz University, DSR, Jeddah, Saudi Arabia.

What is claimed is:

1. A computer-implemented contactless method for simultaneously measuring, from a video of a subject, at least an oxygen saturation level, a blood glucose level, and a heart rate of the subject, comprising: capturing by a camera a red-green-blue (RGB) video of the subject, the RGB video being of at least one area of the subject's body selected from the group consisting of at least a part of a head of the subject, at least a part of an arm of the subject, and at least a part of a leg of the subject; inputting the RGB video of the subject to a non-transitory computer readable memory of a data processor associated with said camera, configured with calibration parameters for computation of oxygen saturation levels using RGB videos captured by said camera; decomposing, with the data processor, the RGB video into a red band signal, a green band signal, and a blue band signal; generating with the data processor, a measurement of the oxygen saturation level of the subject using said calibration parameters, the red band signal and the blue band signal from the decomposed RGB video; simultaneously generating with the data processor a measurement of the blood glucose level of the subject, using said green band signal by generating a three-dimensional (3D) RGB matrix from said RGB video; wherein the 3D RGB matrix is generated by combining the red band signal, the blue band signal, and the green band signal generating a one-dimensional (1D) photoplethysmogram (PPG) signal by a 3D to 1D dimensional reduction of the 3D RGB matrix, creating a blood glucose level measurement model, by steps comprising evaluating, with the data processor, a relationship between the green band signal and the 1D PPG signal, and generating with the data processor the measurement of the blood glucose level of the subject using the blood glucose level measurement model; simultaneously generating with the data processor the heart rate measurement of the subject by steps comprising calculating peaks in the 1D PPG signal; and displaying in real time, on a display communicatively coupled to the data processor, the generated measurement of the oxygen saturation level of the subject, the generated measurement of the blood glucose level of the subject, and the generated heart rate measurement of the subject.

2. The method of claim 1, further comprising a step of recording, into memory, data representing the measurement of the blood glucose level of the subject, the measurement of the heart rate of the subject, and the measurement of the oxygen saturation level of the subject, and wherein the displaying of the measurement of the blood glucose level, the heart rate and the oxygen saturation level of the subject is on a display screen of a mobile device.

3. The method of claim 1, wherein the capturing of the RGB video by the camera comprises capturing light that reflects from or is transmitted through the at least one area of the subject's body.

4. The method of claim 3, wherein the at least one area of the subject's body is a face.

5. The method of claim 3, wherein the at least one area of the subject's body is a finger, a palm, or an earlobe.

6. The method of claim 1, further comprising generating by the data processor, based on the green band signal, a measurement of variation of the subject's heart rate, simultaneously with the generating of the blood glucose level, the oxygen saturation level, and the heart rate of the subject, wherein the displaying step simultaneously displays the generated measurement of the heart rate, the variation in heart rate, the blood glucose level, and the oxygen saturation level of the subject.

7. A system for implementing the method of claim 1, the system comprising: at least one camera configured to obtain RGB video, the at least one camera being a mobile phone camera of a mobile device; at least one light source configured to provide light that reflects from or is transmitted through tissue of the subject, wherein the at least one light source is a LED mobile phone flash of the mobile device; at least one computer; and at least one monitor or screen to display the simultaneously generated oxygen saturation level, blood glucose level, and heart rate of the subject.

\* \* \* \* \*